United States Patent
Gabourie (12)

(10) Patent No.: US 6,197,066 B1
(45) Date of Patent: Mar. 6, 2001

(54) PROSTHETIC FOOT PROVIDING PLANTAR FLEXION AND CONTROLLED DORSIFLEXION

(76) Inventor: Robert Maurice Gabourie, R.R. #1, Fonthill, Ontario (CA), L0S 1E6

( * ) Notice: Subject to any disclaimer, the term of this patent is extended or adjusted under 35 U.S.C. 154(b) by 0 days.

(21) Appl. No.: 09/399,174

(22) Filed: Sep. 20, 1999

(30) Foreign Application Priority Data

Jul. 6, 1999 (CA) .................................................. 2277451

(51) Int. Cl.[7] ........................................................ A61F 2/66
(52) U.S. Cl. .............................................. 623/52; 623/55
(58) Field of Search .................................. 623/53, 52, 55

(56) References Cited

U.S. PATENT DOCUMENTS

| 5,116,383 | * | 5/1992 | Shorter et al. | ........................... 623/49 |
| 5,507,838 | * | 4/1996 | Chen | ....................................... 623/55 |
| 5,944,760 | * | 8/1999 | Christensen | .............................. 623/55 |

FOREIGN PATENT DOCUMENTS

9304552  *  7/1995  (BR) ....................................... 623/55

* cited by examiner

Primary Examiner—David H. Willse
(74) Attorney, Agent, or Firm—Freedman & Associates (57) ABSTRACT

The present invention relates to a prosthetic foot including an integral spring portion providing motion in the foot, particularly a unitary foot structure providing a selectable degree of plantar flexion and a stiff structure for toe off. The present invention has found that an integrally formed c-shaped spring portion having an anterior gap, joining a connection platform and the heel and forefoot portions can provide a controlled range of natural mobility in a prosthetic foot as an economical design. The c-shaped spring can deflect, angling the connection platform rearwardly to a partially opened position against the bias of the spring, and angling the connection platform forwardly until the stop abuts the top surface of the forefoot in a closed position. The stop is positioned a selected distance above the top surface to obtain the desired angle of dorsiflexion. The plantar flexion against the bias of the spring is relatively stiff and provides a variable limit to the range of plantar flexion depending on the force exerted. In contrast, the deflection closing the c-shaped spring is relatively compliant but provides an angular range specifically defined by the position of the stop. In addition, the anterior gap also deflects to permit more limited inversion and eversion before the deflection is stabilized by contact between the stop and the top surface. Additional flexibility is obtained using an integral spring element having a substantially S-shape. The posterior facing c-shaped aperture in the S-shaped spring element provides additional deflection for plantar flexion.

14 Claims, 7 Drawing Sheets

PROSTHETIC FOOT PROVIDING PLANTAR FLEXION AND CONTROLLED DORSIFLEXION

FIELD OF THE INVENTION

This invention relates to a prosthetic foot including an integral spring portion providing motion in the foot, particularly a unitary foot structure providing a selectable degree of plantar flexion, dorsiflexion and a stiff structure for toe off.

BACKGROUND OF THE INVENTION

The prosthetic limb and foot devices which have been available have either severely limited the mobility of the user, or have sought to reconstruct the complex foot and ankle structure through the use of very complex prosthetic structures to simulate a human gait. Unfortunately, a significant need for prosthetic limbs has been created in underdeveloped countries by recent conflicts and the widespread use of landmines. In these places having the greatest need, the use of complex prosthetic devices is made impossible by the high cost. Only the simplest prosthetic designs are affordable. The lack of motion in the foot of these designs, such as the SACH (solid ankle cushion heel) foot or the Jaipur foot, cause restrictions to mobility, particularly over rough terrain. The cost of the SACH foot and the long fabrication time of the Jaipur foot have meant that these devices are unable to address the current need. In addition to high cost and poor mobility, prior prosthetic designs have been susceptible to damage by water, and to material fatigue over undesirably short periods.

A prosthetic foot which attempts to simulate a human gait is disclosed in U.S. Pat. No. 4,645,509 issued to Model and Instrument Development Corporation Feb. 24, 1987. This device includes a resilient cantilever spring bonded to a surrounding low density material. The cantilever spring is designed to provide energy return, particularly for active use. Impact at the heel is reduced due to the low density material designed to provide heel cushioning. Flexure of the cantilever spring during plantar flexion is limited by the rigidity of the spring material. The end of the cantilever element is upturned, corresponding to the ball of a foot, to reduce stress on the keel during toe off. This cantilever device does not provide a stable structure for toe off. The design necessarily causes strain between the high and low density materials, in addition to the complexity and cost of manufacture. A further difficulty of this design is that the stiffness appropriate for energy return during active use may be too resistant for normal walking.

U.S. Pat. No. 4,555,817 issued to Roderick W. McKendrick incorporates flexibility by interconnecting a plurality of elements with a cable. A compressible rubber block is positioned between substantially rigid elements in the heel region to add flexibility and to provide resilience to return the elements to their original positions. The tension of the cable can be adjusted to permit more or less flexibility for rotation, lateral, and medial movements and plantar and dorsiflexion. Numerous parts must be assembled adding significant expense, and the flexibility imparted by wood, leather and rubber parts are subject to wear and hardening. In addition, plantar flexion is created by the loose connection of the cable and relative sliding movement. The range of plantar flexion or dorsiflexion is no greater than permitted lateral movements and thus normal movement for walking is restricted.

A further example of a flexible prosthesis is disclosed in U.S. Pat. No. 5,219,365 issued to Sabolich Inc., Jun. 15, 1993. Flexibility is primarily created by a highly arched keel. Additional flexibility for plantar flexion and dorsiflexion is introduced by a horizontal slot in the ankle portion. The keel is under constant pressure putting significant stress on the prosthetic material. The heel and toe portions spread apart with the pressure of each step causing an unnatural motion in the foot, and significant strain to the cosmetic covering. The keel design does not ever provide a stiff platform from which to toe off. The horizontal slot for increasing plantar flexion and dorsiflexion mobility is positioned in the rear of the ankle portion. As a result, no stop limits the dorsiflexion range to an appropriate toe off position.

U.S. Pat. No. 4,792,340 issued to Ernest M. Burgess in 1988 discloses a prosthetic ankle having a precisely formed kerf as a flexure joint. The flexibility of the ankle joint is very limited, intending to be used with a prosthetic foot having enhanced flexure characteristics. The kerf includes a double convolute section the surfaces of which contact each other to limit movement. The kerf provides narrow controlled limits to plantar flexion, dorsiflexion, axial rotation, inversion and eversion. Once the limit is met, the ankle structure becomes rigid in each direction and provides no further cushioning. In addition, the kerf including double convolute curves is difficult to manufacture, and on its own cannot provide the flexibility needed for a normal gait, particularly over uneven ground. The costs of combining a complex foot design and a complex ankle design are out of reach of the majority of patients in need of a prosthetic limb.

It is an object of the invention to provide a simple and economical foot prosthesis which simulates human movement by providing a controllable range of plantar flexion, dorsiflexion, inversion and eversion. Flexibility in the foot provides significant advantages in mobility over a simple rolling motion. The prosthesis is advantageously light weight and resistant to wear.

SUMMARY OF THE INVENTION

The present invention has found that an integrally formed c-shaped spring portion having an anterior gap, joining a connection platform and the heel and forefoot portions can provide a controlled range of natural mobility in a prosthetic foot as an economical design. In a further embodiment of the invention an additional oppositely facing c-shaped spring portion provides additional flexibility control.

In accordance with the invention there is provided a prosthetic foot comprising:

a foot portion of resilient material including a heel and a forefoot;

a connection platform for engaging a shank, flexibly secured to the foot portion, defining a substantially c-shaped aperture between them including a substantially horizontal anterior gap, whereby the connection platform is deflectable between a rearwardly angled position, and a forwardly angled position limited to a selected angle where the connection platform abuts the forefoot closing the anterior gap, thereby permitting the foot to plantar flex varying in response to load during heel strike, and to dorsiflex to a selected angle prior to toe off.

In a further embodiment of the present invention there is provided a prosthetic foot as further including a substantially c-shaped posterior aperture between the connection platform and the heel having a substantially horizontal posterior gap for providing additional flexibility control for plantar flexion.

In a still further embodiment of the present invention there is provided a prosthetic foot comprising:

a foot portion of resilient material including a heel and a forefoot and an arched keel between them, the forefoot having a top surface above the arched keel;

a connection platform, for engaging a leg assembly, flexibly secured above the foot portion at a selected position between the heel and a toe;

a stop member on the platform spaced a selected distance from the top surface of the forefoot adapted to abut the top surface, for providing a selected angle of dorsiflexion, and limited inversion and eversion in use; and, a spring joining the connection platform to the foot portion for flexible movement between an open rearwardly angled position for a range of plantar flexion to provide cushioning during heel strike, and a forwardly angled position abutting the top surface of the forefoot to provide stiffness during toe off, and further providing a fixed connection between the platform and the foot portion for support in a neutral position.

In accordance with the present invention a further embodiment further comprises a prosthetic foot wherein the spring joining the platform to the foot forms an S-shaped joining element having an anterior substantially horizontal gap and a posterior substantially horizontal gap for deflection to provide plantar flexion and dorsiflexion in use, and wherein the stop member provides a constriction of the anterior gap.

Advantageously, the prosthetic foot of the present invention emulates natural foot and ankle movement, particularly by moving the plantar flexion axis closer to the natural ankle. As a further advantage the foot is constructed as a unitary device without requiring additional mechanisms to provide complex movement creating an affordable device.

BRIEF DESCRIPTION OF THE DRAWINGS

Exemplary embodiments of the invention will now be described in accordance with the drawings in which.

Like numerals are used throughout to designate like elements.

DETAILED DESCRIPTION OF THE INVENTION

Figure 1:
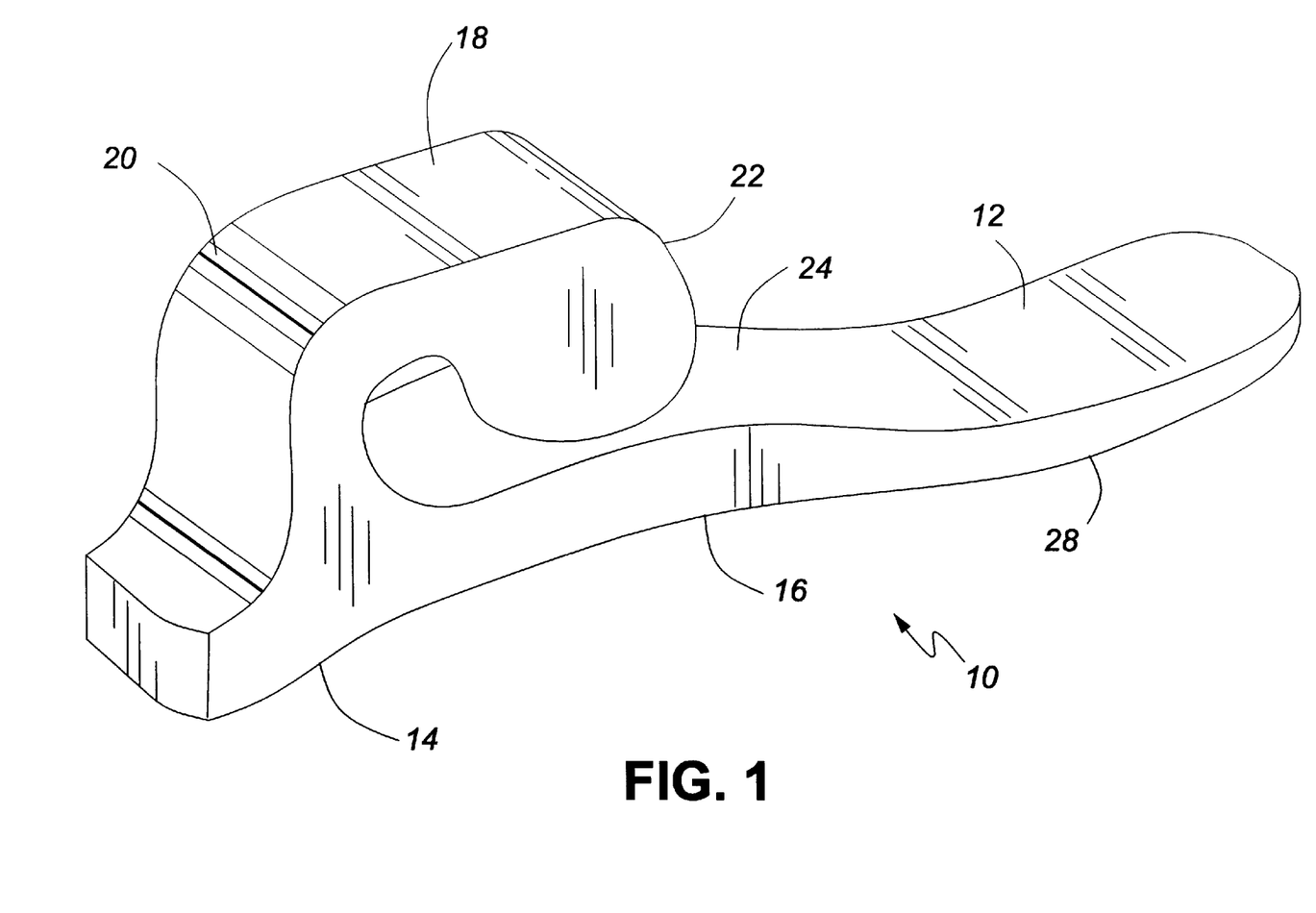
FIG. 1 is an isometric view of a prosthetic foot in accordance with the present invention.
Figure 2:
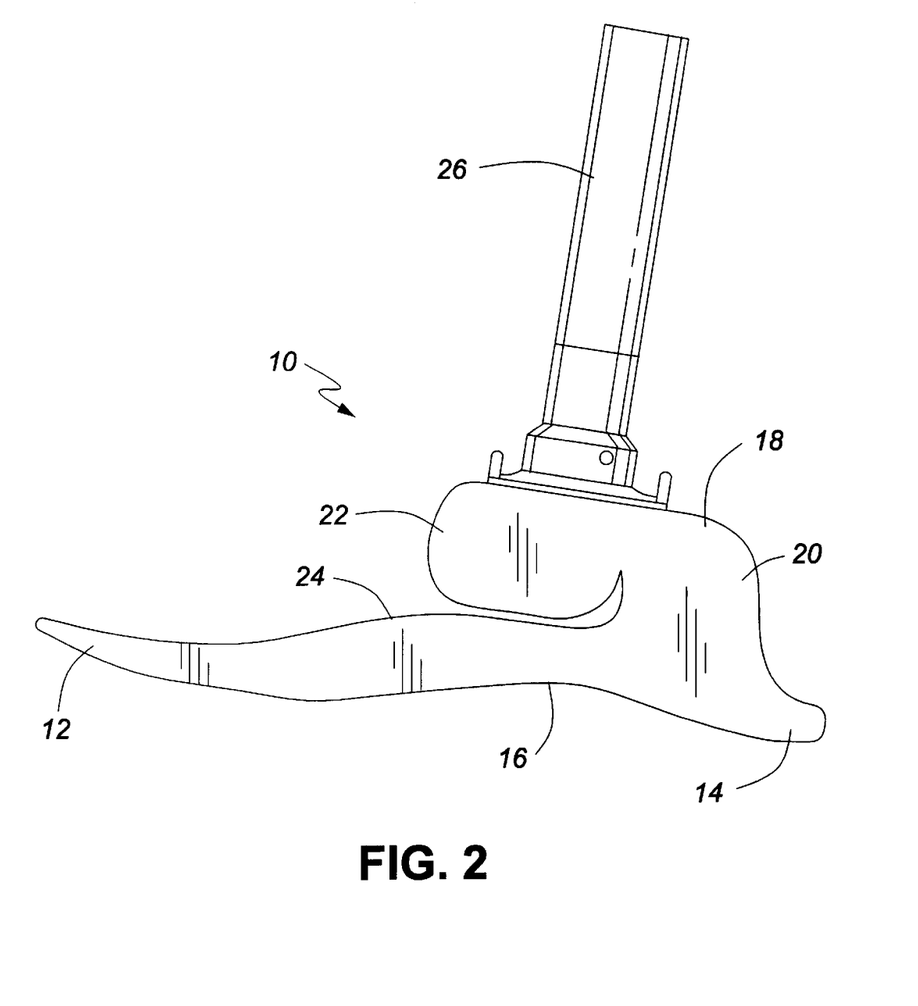
FIG. 2 is an isometric view of a prosthetic foot in accordance with the present invention including a shank connected to the prosthetic foot.

The prosthetic foot, shown generally at 10 in FIG. 1, includes a forefoot portion 12 and a heel portion 14 joined together by an arched keel 16. A connection platform 18 for securing a shank or leg element 26 (shown in FIG. 2) is secured to the foot 10 by an integral spring 20. A stop 22 projects downwardly at the front of the connection platform 18. The stop 22 is spaced above a top surface 24 of the forefoot portion 12. The integral spring 20 joins the connection platform 18 to the foot 10 in advance of the heel portion 14 forming a c-shaped aperture 21 having an anterior gap 25 (seen clearly in FIG. 3). The connection platform 18 includes taps for screw mounts or a standard bolt connection for securing an appropriate shaft 26, and can be adapted to be compatible with a number of commonly used systems. The prosthetic foot 10 may be adapted for use with different culturally suitable cosmetic coverings which do not affect the performance of the foot 10.

Figure 3:
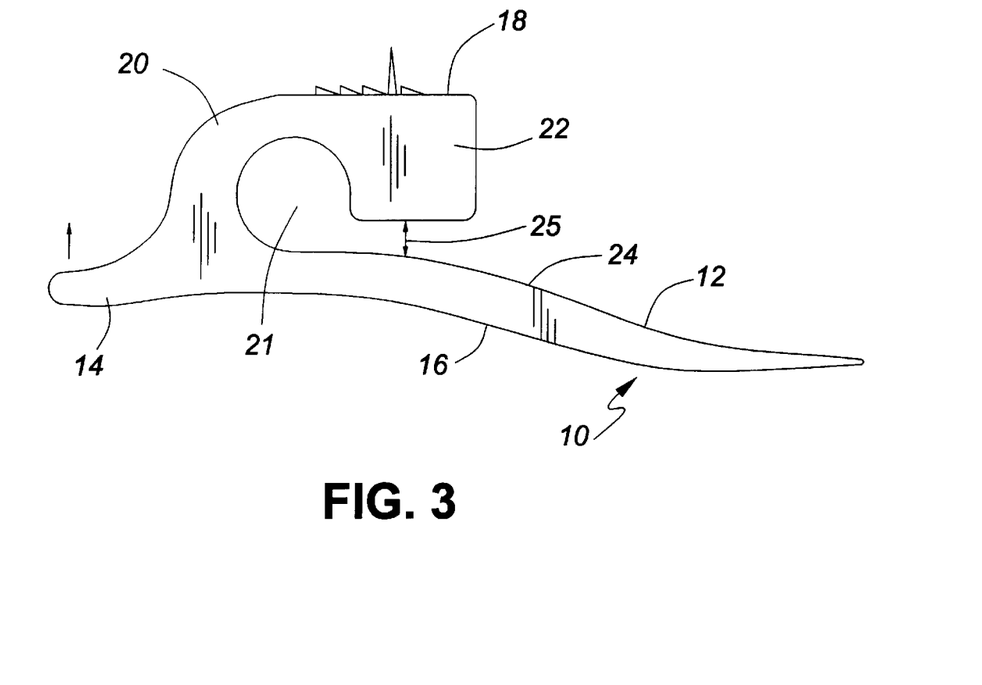
FIG. 3 is a side view of an alternative embodiment of the present invention illustrating a deflection during heel strike.

The spring 20 can deflect, angling the connection platform 18 rearwardly to a partially opened position increasing the anterior gap 25 against the bias of the spring 20, and angling the connection platform 18 forwardly until the stop 22 abuts the top surface 24 of the forefoot 12 closing the anterior gap 25. The stop 22, or the lower surface of the platform 18 itself, is positioned a selected distance above the top surface 24 to obtain the desired angle of dorsiflexion. The plantar flexion against the bias of the spring 20 is relatively stiff and provides a variable limit to the range of plantar flexion depending on the force exerted. In contrast, in deflection closing the anterior gap 25 of the c-shaped aperture 21, the spring 20 is relatively compliant but provides an angular range specifically defined by the position of the stop 22. In addition, the anterior gap 25 also deflects to permit more limited inversion and eversion before the deflection is stabilized by contact between the stop 22 and the top surface 24 This too can be controlled by varying the shape of the stop 22.

The keel 16 provides additional flexibility and cushion. Preferably, the stop 22 abuts the top surface 24 directly above the apex of the arch of the keel 16 flexing the keel 16 and providing additional energy return on toe off. The heel portion 14 projects to provide a stable base curved upward to facilitate rolling movement. The forefoot 12 is generally symmetrical along the longitudinal axis, meaning that right and left are interchangeable. The toe at the tip of the forefoot 12 is upturned slightly and can be adjusted in taper and thickness for additional flexibility. In addition the forefoot can be formed in left and right models to have varying thickness in lateral areas, as known in the art, or to include longitudinal slots to add lateral flexibility.

Figure 4:
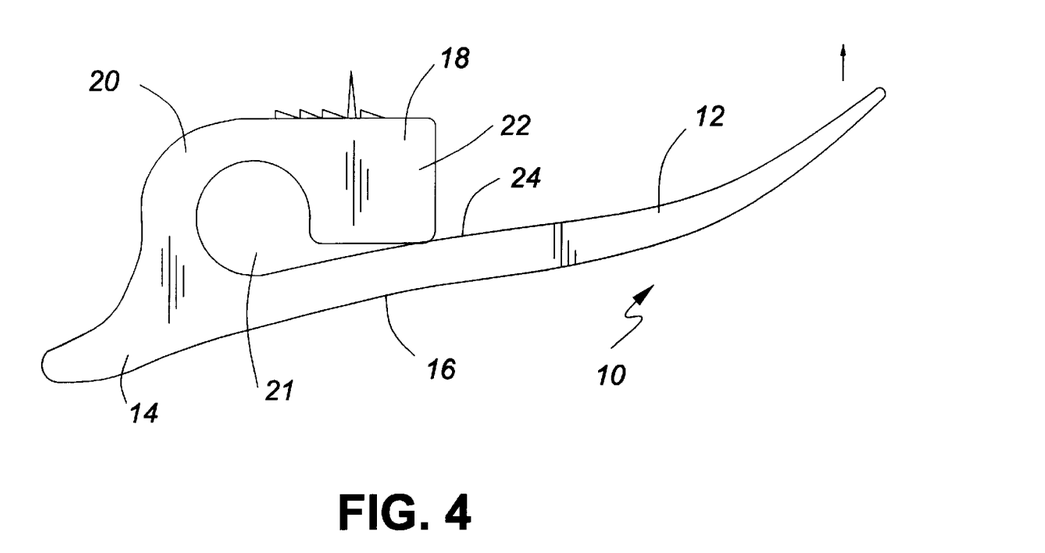
FIG. 4 is a side view of the embodiment of FIG. 3 illustrating a deflection during toe off.

The hinge motion of the spring 20 simulates the human gait. During heel strike, shown in FIG. 3, plantar flexion of the forefoot 12 occurs opening the c-shaped aperture 21 and providing heel cushion. The spring 20 is biased to spring back elastically from the open heel strike position, and the energy return serves to accelerate movement to a flatfoot position. The spring 20 compresses to provide dorsiflexion as the foot rolls toward toe off. When the anterior gap 25 is closed and the stop 22 abuts the top surface 24 of the forefoot 12, the prosthetic foot 10 provides a stiff stable platform for toe off, shown in FIG. 4. It is important that the foot 10 be as stiff as possible at toe off, in order to provide a stable base for the lower limb from which forward thrust can take place. The compliance of the design and the range of deflection also provide control over the amount of lateral movement, inversion and eversion, which assists movement on uneven ground. Advantageously, the design of the present invention exerts less torque on the limb than previous designs due to the relatively free plantar flexion.

Figure 5:
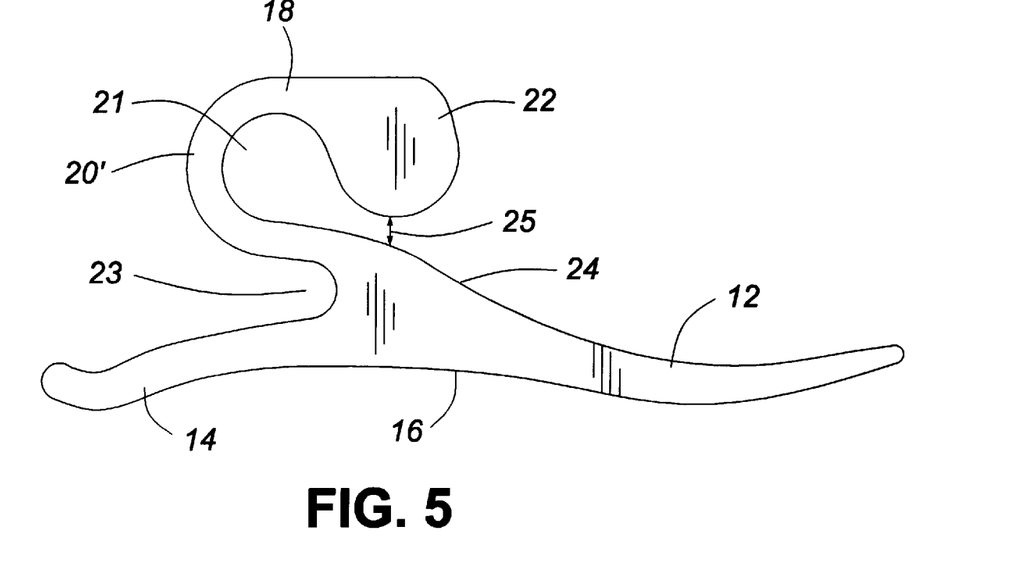
FIG. 5 is a side view of an alternative embodiment of the present invention including an opposite facing c-shaped spring for plantarflexion.
Figure 6:
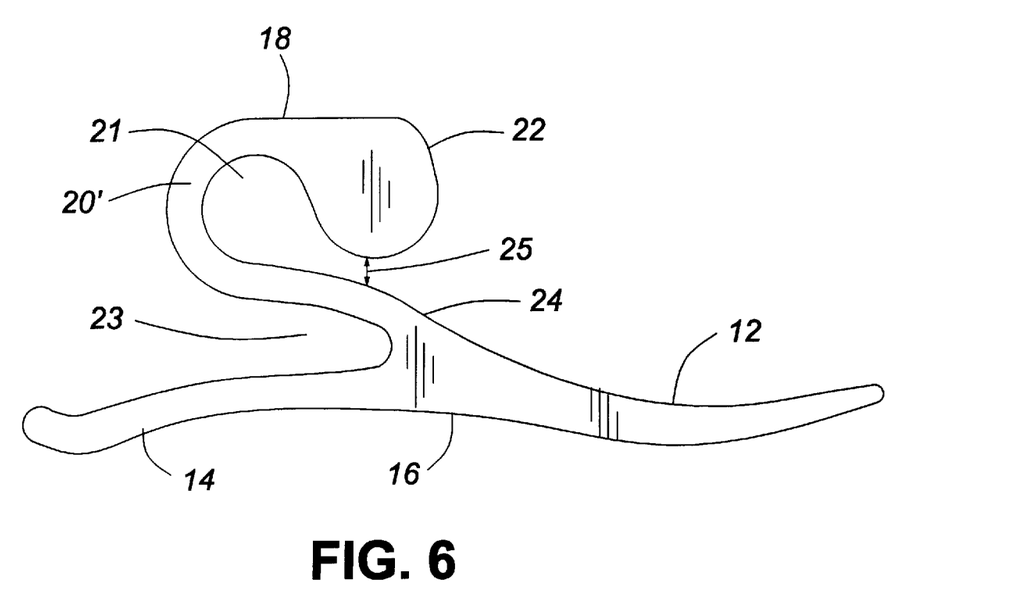
FIG. 6 is a side view of a variation in the design of FIG. 5.

FIGS. 5 and 6 illustrate a further preferred embodiment incorporating an additional oppositely facing c-shaped aperture 23 defined by the spring element 20' for providing more flexibility control during plantar flexion. In this design the plantar flexion can be increased over prior art designs. The torque on the limb is thus significantly reduced. As in FIG. 1 the spring element 20' defines a c-shaped aperture 21 which cooperates with the stop 22 or has an anterior gap 25 to provide a fixed range of dorsiflexion. The oppositely facing c-shaped aperture 23 also defined by the spring element 20' provides greater plantar flexion. The spring element 20' can be formed integrally as a substantially S-shaped element. The posterior c-shaped aperture 23, in addition to the reverse flexion on the anterior c-shaped aperture 21, provides a stiff but variable limit to the range of plantar flexion depending on the force exerted. Similarly the spring element 20' can be reversed as a Z-shaped element, still including a stop 22 or controlled anterior gap to obtain the desired angle of dorsiflexion between a posteriorly facing c-shaped aperture and the foot 10. A relatively stiff thermoplastic material, such as having a 2–3 GPa is preferred for reducing weight and providing more energy return and longevity. This double-c or S design provides good flexibility control, particularly for a stiffer material construction. The posteriorly facing c-shaped aperture 23 may vary in depth beneath the spring element 20' as illustrated in FIGS. 5 and 6 to provide additional design control for greater or less flexibility.

Testing on models as shown in FIG. 5 was conducted for varying material elasticity under the following conditions: a Young's modulus of 1000–3000 MPa and a Poisson ratio of 0.43. The shaft is connected through a hole in the connection platform centered at the deepest point on the stop. The models were subjected to a load of 700 N applied to the most distal point in the heel region at an angle 15 degrees anterior to the tibial axis to simulate heel strike. Similarly, toe off was simulated subjecting the models to a load of 700 N applied midway between the metatarsal head and the distal end of the phalanges at an angle 45 degrees posterior to the tibial axis.

The results in the following table show maximum angle deflection in degrees for plantar flexion of the tested models:

| Plantar Flexion | |
| --- | --- |
| Young's Modulus | Maximum Angle |
| 1000 | 29.008 |
| 1580 | 20.593 |
| 2550 | 9.950 |
| 3000 | 8.192 |

Figure 7A:
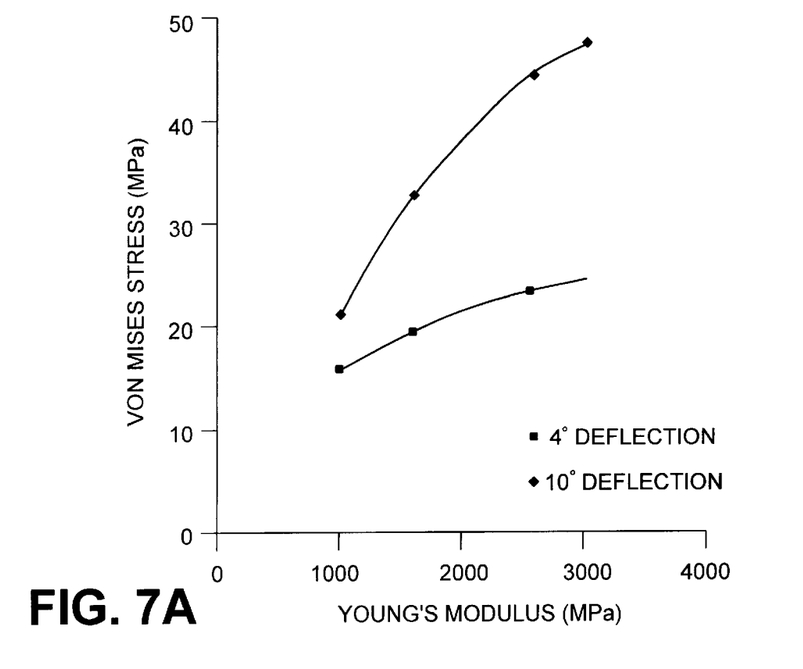
FIG. 7A is a graph of von Mises Stress versus Young's Modulus illustrating the test results of the models in accordance with FIG. 5.
Figure 7B:
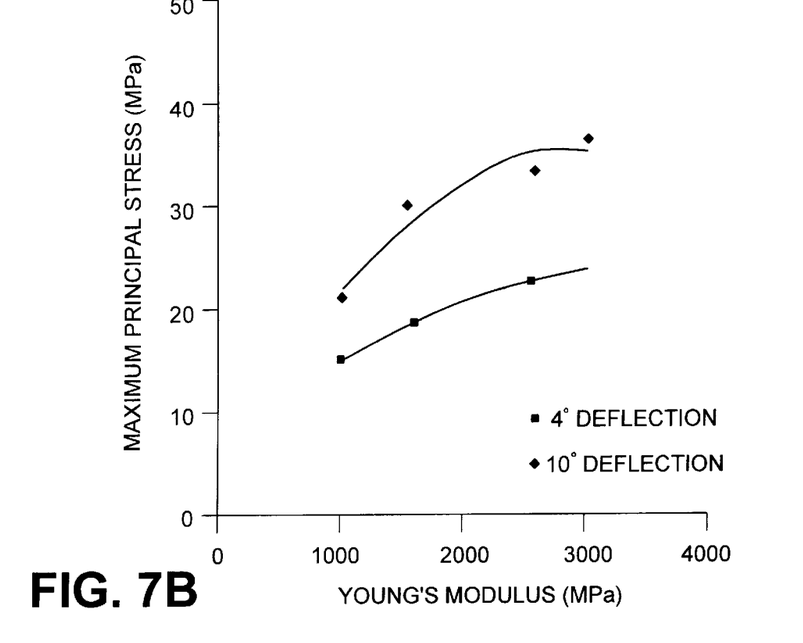
FIG. 7B is a graph of maximum Principal Stress illustrating the test results of the models in accordance with FIG. 5.
Figure 7C:
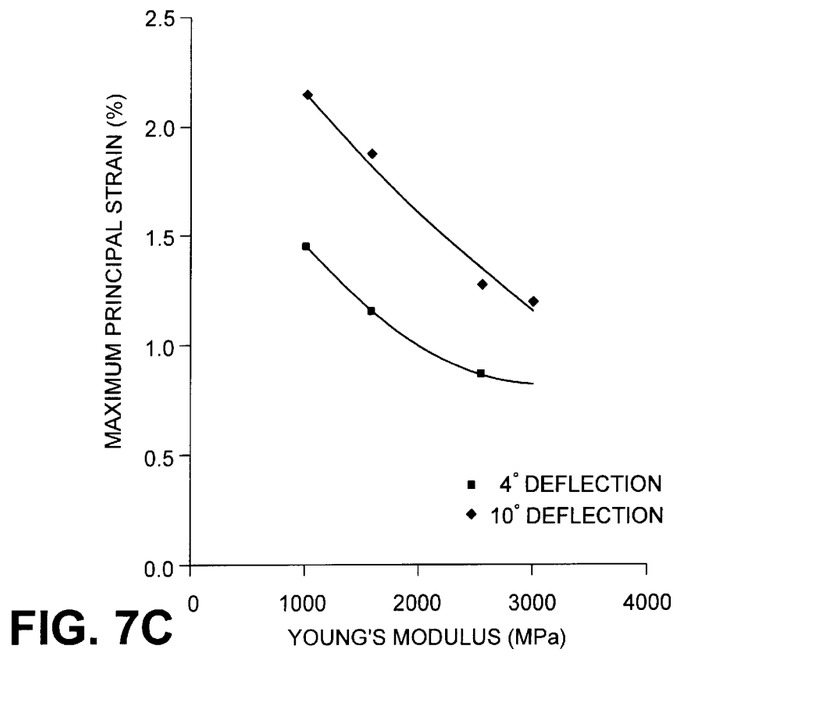
FIG. 7C is a graph of Maximum Strain illustrating the test results of the models in accordance with FIG. 5.

In addition, von Mises stress, maximum principal stress and maximum principal strain were recorded as shown in the design curves in FIGS. 7A–7C.

Dorsiflexion is recorded for different models as shown in FIG. 5, each having a varying anterior gap and each having a Young's Modulus of 2550 MPa. An average stiffness and an apparent stiffness are recorded. Average stiffness is the stiffness observed if no displacement occurred before contact. Apparent stiffness takes into account the displacement that occurs before contact. The models tested have progressively smaller anterior gaps. Each model uses the same keel curvature and forefoot, heel and spring material thickness. The model illustrated in FIG. 5 has the largest anterior gap. A model A has a smaller anterior gap. And a model B has the smallest anterior gap of the three tested.

|  | FIG. 5 | A | B |
| --- | --- | --- | --- |
| Average stiffness | 14.503 kN/m | 32.844 kN/m | 43.835 kN/m |
| Apparent stiffness | 15.295 kN/m | 37.209 kN/m | 51.972 kN/m |

Figure 8:
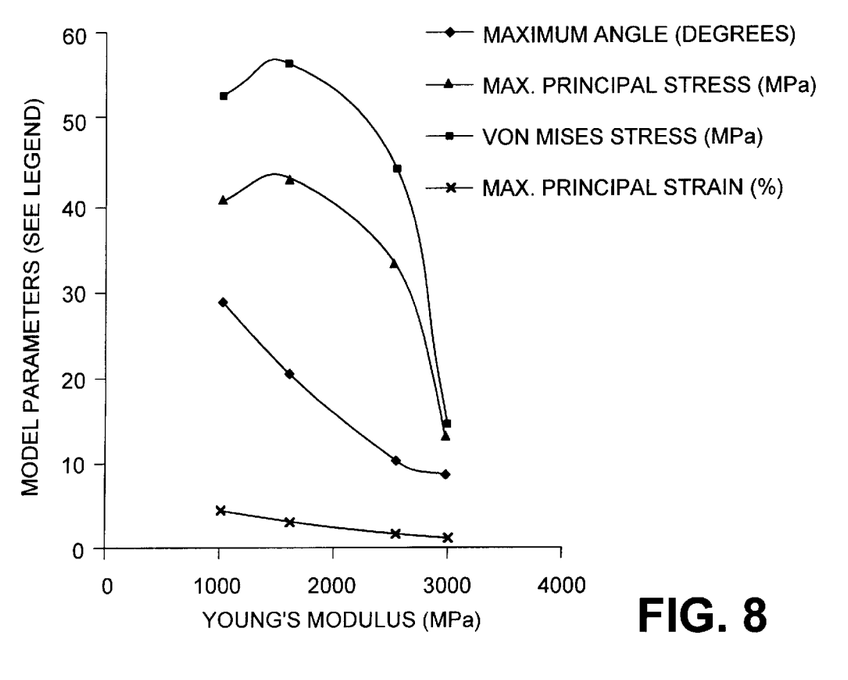
FIG. 8 is a graph of a performance summary illustrating Maximum Angle, Maximum Principal Stress, von Mises Stress, and Maximum Principal Strain for testing of the embodiment illustrated in FIG. 5; and, FIG. 9 is a side view of a variation of the design of FIGS. 5 and 6.

Testing on the design shown in FIG. 6, having a deeper c-shaped aperture 23 for plantar flexion and a Young's modulus of 3000 MPa resulted in a maximum angle of 15.560 degrees. In addition, von Mises stress, maximum principal stress and maximum principal strain are shown in the performance curves of FIG. 8.

The results above, and the graphic illustrations in FIGS. 7A–7C and FIG. 8, show how design parameters can be adapted to control the prosthetic foot 10 performance. Control of the amount of plantar flexion can be achieved by the placement of the shank 26 anteriorly or posteriorly; the anterior or posterior placement of the stop 22; or the depth of the posterior c-shaped aperture. A thicker midfoot portion also contributes to a stiffer design.

For all designs an initial soft phase is followed by a stiffer or more rigid response. Design variations can also control these performance characteristics such as the force necessary to deflect the soft phase and the stiffer phase affecting the total deflection in each phase and the energy recovery.

Parametric analysis using a computer has enabled numerous iterations of the initial design. From this it has been determined that the size of the fillet forming the integral spring 20' between the c-section 23 and the heel portion 14 is highly sensitive to the amount of deflection the foot can achieve. A small decrease in the radius dramatically increases the amount of deflection. Upon analyzing the stiffness at toe off, another critical parameter was determined. The distance between the stop 22 and the upper surface 24 of the foot 10 is crucial in the compliance characteristics upon toe off. Small decreases in the distance before contact significantly increase the stiffness of the toe portion 12 of the foot 10.

Both the fillet size and the travel distance before contact are important characteristics for this foot design. Since the target population for this prosthetic foot lives in developing countries, a simple way to customize one design for thousands of people was critical. The removal of a small amount of material from a design as shown in FIG. 5, for example, to decrease the radius of the fillet, increases the amount of deflection the foot can achieve. Similarly, by removing a small amount of material to increase the distance before contact occurs, the foot can be made more compliant upon toe off. These two simple modifications will enable people of varying weight to enjoy the same performance characteristics that other prosthetic foot designs cannot provide.

Figure 9:
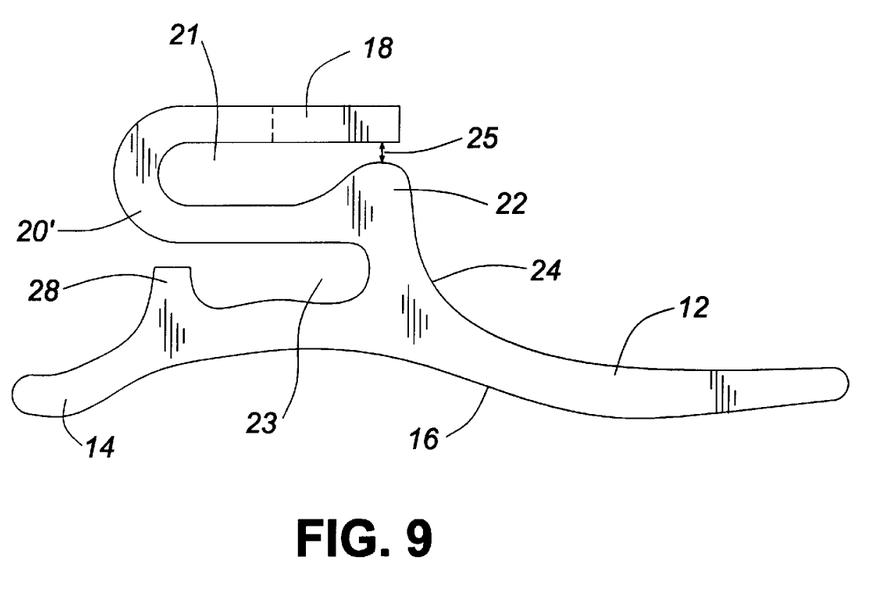

FIG. 9 illustrates a further embodiment in accordance with the invention the stop 22 positioned on the top surface 24 of the forefoot portion 12 to constrict the anterior gap, rather than depending from the connection platform 18. The connection platform 18 and stop 22 define between them the anterior gap 25 for the desired angle of dorsiflexion. In addition this embodiment includes the additional oppositely facing c-shaped aperture 23, as shown in FIGS. 5 and 6, to provide additional flexibility to plantar flexion. In this embodiment, however, the oppositely facing c-shaped aperture 23 includes a stop 28 to provide an absolute limit for the angle of plantar flexion. Of course, numerous other stop designs could be used, for instance to facilitate manufacture, as long as a stable contact is made between the platform 18 and the upper surface 24 of the foot 10 for toe off.

Performance of the prosthetic foot design may be altered while still providing the desired mobility of the present invention. The position of the shank connection to the foot 10 may be varied anteriorly for a more compliant design, or posteriorly for a stiffer design. The position of the stop 22 as it abuts the top surface 24 may also be disposed anteriorly for a more compliant design or posteriorly for a stiffer design. The thickness of the foot 10 at the abutment of the stop 22, and the arch of keel 16 also control the degree of deflection. It is understood that the stop 22 may be placed below the connection platform 18 or above the top surface 24, its purpose being to constrict the anterior gap and thus control the range of dorsiflexion prior to abutting the top surface 24 for toe off. The spring 20 or 20' is secured to the foot at a balance point preferably for a neutral standing position. The bolt connection for the shaft 26 is generally positioned approximately 35% forward of the posterior of the foot 10. This position may also be moved anteriorly or posteriorly to alter the balance and hence the gait.

Choice of material will also affect the stiffness of the design. A preferred material is a thermoplastic such as polypropylene, acetol, nylon etc., suitable for injection molding, water jet molding or extrusion. Generic polypropylene was modeled in the design using a Young's modulus of 2–3 GPa and a Poisson's ratio of 0.43. These values are representative of a broad range of materials suitable for this application. An injection molding process including removable pins to form a honeycomb structure is contemplated to produce a prosthetic of light weight. Alternatively, the prosthetic can be extruded continuously and cut for final shaping. The integral design requires no assembly and relatively simple manufacture, making the foot available inexpensively to areas of highest need. One embodiment includes attachment sites in the molded foot for easily attaching the cosmetic cover. The use of resilient plastic materials offers good control of flexibility and resistance to wear. Plastics also provide easy care and resistance to water damage.

The above-described embodiments of the invention are intended to be examples of the present invention and numerous modifications, variations, and adaptations may be made to the particular embodiments of the invention without departing from the scope and spirit of the invention, which is defined in the claims.

What is claimed is:

1. A prosthetic foot comprising:
   a foot portion of resilient material including a heel, a forefoot and an arched keel between them;
   a connection platform for engaging a shank, flexibly secured to the foot portion, defining a substantially c-shaped aperture between them including a substantially horizontal anterior gap, the connection platform being joined to the foot portion in advance of the heel, and wherein
   the connection platform is deflectable between a rearwardly angled position, and a forwardly angled position limited to a selected angle where the connection platform abuts the forefoot closing the anterior gap, thereby permitting the foot to plantar flex varying in response to load during heel strike, and to dorsiflex to a selected angle prior to toe off.

2. A prosthetic foot as defined in claim 1, wherein the foot portion and connection platform comprise a unitary construction including an integral spring.

3. A prosthetic foot as defined in claim 2, wherein the unitary construction is formed of a resilient plastic.

4. A prosthetic foot as defined in claim 3, further including a substantially c-shaped posterior aperture between the connection platform and the heel having a substantially horizontal posterior gap for providing additional flexibility control for plantar flexion.

5. A prosthetic foot as defined in claim 4, wherein the posterior aperture is disposed below the c-shaped aperture including a substantially horizontal anterior gap.

6. A prosthetic foot as defined in claim 2, further including a stop means between the connection platform and the foot portion restricting the anterior gap for controlling the selected angle where the connection platform abuts the forefoot closing the anterior gap.

7. A prosthetic foot as defined in claim 6, wherein the stop means comprises a depending element integral with an anterior portion of the connection platform.

8. A prosthetic foot as defined in claim 6, wherein the arched keel has an apex in the forefoot positioned in alignment with the stop means.

9. A prosthetic foot as defined in claim 8, wherein the forefoot includes a flexible toe portion having a curved base for rolling movement.

10. A prosthetic foot as defined in claim 9, further including a projecting flexible heel portion having a curved base for rolling movement.

11. A prosthetic foot comprising:
    a foot portion of resilient material including a heel and a forefoot and an arched keel between them, the forefoot having a top surface above the arched keel;
    a connection platform, for engaging a leg assembly, flexibly secured above the foot portion at a selected position between the heel and a toe;
    a stop member on the platform spaced a selected distance from the top surface of the forefoot adapted to abut the top surface, for providing a selected angle of dorsiflexion, and limited inversion and eversion in use; and,
    a spring joining the connection platform to the foot portion in advance of the heel for flexible movement between an open rearwardly angled position for a range of plantar flexion to provide cushioning during heel strike, and a forwardly angled position abutting the top surface of the forefoot to provide stiffness during toe off, and further providing a fixed connection between the platform and the foot portion for support in a neutral position.

12. A prosthetic foot as defined in claim 11, comprising a unitary structure of resilient material.

13. A prosthetic foot as defined in claim 11, wherein the spring joining the platform to the foot forms an S-shaped joining element having an anterior substantially horizontal gap and a posterior substantially horizontal gap for deflection to provide plantar flexion and dorsiflexion in use, and wherein the stop member provides a constriction of the anterior gap.

14. A prosthetic foot as defined in claim 13, further including a posterior stop member on the heel adapted to abut the S-shaped joining element, for providing a selected angle of plantar flexion in use.

\* \* \* \* \*